US006751294B1

United States Patent
Blish II et al.

(10) Patent No.: US 6,751,294 B1
(45) Date of Patent: Jun. 15, 2004

(54) PREVENTION OF PARAMETIC OR FUNCTIONAL CHANGES TO SILICON SEMICONDUCTOR DEVICE PROPERTIES DURING X-RAY INSPECTION

(75) Inventors: Richard C. Blish II, Saratoga, CA (US); Susan Xia Li, Fremont, CA (US); David S. Lehtonen, Austin, TX (US); J. Courtney Black, San Jose, CA (US); Don C. Darling, San Jose, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 10/215,075

(22) Filed: Aug. 8, 2002

(51) Int. Cl.[7] .............................................. G21K 3/00
(52) U.S. Cl. ..................................... 378/156; 250/505.1
(58) Field of Search .......................... 378/53, 57, 156, 378/157, 158, 159; 250/505.1

(56) References Cited

U.S. PATENT DOCUMENTS 4,910,757 A * 3/1990 Kiyasu et al. ................. 378/53
RE35,423 E * 1/1997 Adams et al. ................. 378/58
6,597,758 B1 * 7/2003 Rosner ......................... 378/53

OTHER PUBLICATIONS

Elements of X–Ray Diffraction, B.D. Cullity, Addison–Wesley Publishing Co. Inc., published 1956, pp. 1–17.

Filter Optimization for X–ray Inspection of Surface–Mounted ICs, Richard C. Blish II, Susan Xia Li, David S. Lehtonen, IEEE Symposium, Apr. 2002, pp. 377–379.

* cited by examiner

Primary Examiner—Edward J. Glick
Assistant Examiner—Courtney Thomas

(57) ABSTRACT

An apparatus for x-raying a semiconductor device which includes semiconductor material and conductive material, the apparatus including a source of x-rays, a filter for receiving x-rays from the source of x-rays and allowing transmission of x-rays to the device, the filter having an atomic number greater than the atomic number of the conductive material of the device, and an x-ray imager for receiving x-rays from the device.

15 Claims, 9 Drawing Sheets

PREVENTION OF PARAMETIC OR FUNCTIONAL CHANGES TO SILICON SEMICONDUCTOR DEVICE PROPERTIES DURING X-RAY INSPECTION

BACKGROUND OF THE INVENTION

1. Technical Field

This invention relates generally to x-ray inspection of semiconductor devices, and more particularly, to prevention of changes to semiconductor device properties while proper x-ray inspection is achieved.

2. Background Art

In order to maximize the quality of printed circuit board manufacturing process, semiconductor devices, in particular surface mounted devices with "hidden" solder joints to a printed circuit board, typically undergo an x-ray in on. In f thereof, and with reference to FIG. 1 (rotated 90 degrees clockwise from a conventional orientation of elements therein), a semiconductor device 20 is placed on an inspection tray 22 of for example polymer material. Such a typical semiconductor device 20 includes silicon body 24 having a protective coating 25 of molding compound (In FIG. 1 shown lying on the tray 22), the silicon body 24 having active region 24A and inactive region 24B secured to a substrate 26 by a silver-organic material adhesive 28 (wire bonds connecting silicon body 24 and substrate 26 not shown). The substrate 26 includes organic portions 30, 32 (dielectric layers) and patterned copper layers (one shown at 34), which copper layer 34 communicates with the active region 24A of the silicon body 24 (active region 24A approximately one micron (1$\mu$m) in thickness and oriented most adjacent the tray 22) and lead/tin solder balls 36 which connect to a layer of copper traces 38 on an organic material (for example polyimide, epoxy, polyethylene, or glass fiber) board 40, i.e., a printed circuit board or printed wiring board. It will be understood that the particular configuration of the semiconductor device 20 shown is for purposes of illusion, and that such device 20 may be configured in a wide variety of ways, i.e., for example, such semiconductor device may cam a number of levels of copper layers 34 and dielectric layers 30, 32, with appropriate vias connecting the copper layers.

In this example, for purposes of illustration, the following typical thickness values are given:

| | |
|---|---|
| Tray 22: | 400 $\mu$m |
| Molding Compound 25: | 300 $\mu$m |
| Silicon body 24: | 200 $\mu$m (including 1 $\mu$m active region) |
| Silver-organic adhesive 28: | 30 $\mu$m |
| Dielectric layer 30: | 200 $\mu$m |
| Copper layer 34: | 50 $\mu$m |
| Dielectric layer 32: | 200 $\mu$m |
| Solder balls 36: | 400 $\mu$m |
| Copper layer 38: | 50 $\mu$m |
| Printed circuit board 40: | 200 $\mu$m |

During the x-ray inspection, x-rays of a wide range of energies are provided from a source 42 through the tray 22 and into and through the semiconductor device 20, with substantial absorption of x-rays taking place in the copper layers 34, 38 and lead/tin solder balls 36, as compared to the rest of the device, so that proper contrast been the images of the copper layers 34, 38 and solder balls 36 on the one hand, and the rest of the device on the other hand, is provided at image detector 44. In this way, flaws in the copper and/or solder balls can be observed.

During the x-ray inspection process, radiation damage can occur in the silicon body 24. That is, an x-ray beam passing through the silicon body 24 may ionize the silicon, forming electron/hole pairs in the active region 24A, the region approximately 1 $\mu$m thick most adjacent the tray 22. These electrons/hole pairs in the active region 24A can cause undesirable changes in device operating characteristics, and can cause changes to stored charge on device internal nodes or within dielectrics, causing improper operation.

For the following discussion, reference is made to pp. 1–17 of ELEMENTS OF X-RAY DIFFRACTION by B. D. Cullity, Addison-Wesley Publishing Co. Inc., published 1956, which material is herein incorporated by reference.

FIG. 2 is a graph showing x-ray absorption coefficient vs. x-ray energy for silicon, copper, tin and lead, with both axes on a logarithmic scale. As will be sen, and as described in that text, for each material, the general trend of the magnitude of absorption coefficient is downward for increasing levels of x-ray energy, varying as the inverse cube of the energy. In addition, as also described in the text, abrupt, distinctive "edges" occur for each element, corresponding to the characteristic K, L, M, etc. lines of the material. As indicated in the graph of FIG. 2, silicon has a high coefficient of absorption in the x-ray energy range of about 3 KeV (and is therefore highly vulnerable to the problem described above). As illustrated in FIG. 2, the absorption coefficient of silicon drops off significantly as x-ray energy increases, so that the vulnerability of the silicon to this problem decreases substantially with increase in x-ray energy.

FIG. 3 is a graphical representation of the structure of FIG. 1, showing x-ray absorption at the 3 KeV energy level (intensity axis on a logarithmic scale, distance axis on a linear scale). As will be seen, after some absorption by the tray 22 and the molding compound 25, the silicon body 24, including the active region 24A thereof, is exposed to x-ray energy of a high intensity and absorbs a substantial amount of x-ray energy at this energy level (the actual absorption of a body is indicated by the change in intensity of the x-ray entering and passing through the body in accordance with the formula.

$$I_x = I_0 e^{\mu x}$$

where $\mu$=linear absorption coefficient, dependent on material considered, its density, and the wavelength or energy of the incident x-rays $I_0$=intensity of incident x-ray beam, and $I_x$=intensity of transmitted beam after passing through a thickness x (see the above cited text at page 10).

Even though the active region 24A is only approximately 1 $\mu$m thick, as pointed out above, silicon has a high coefficient of absorption at this energy, and there is only the tray 22 and molding compound 25 between the source of x-rays 42 and the active region 24A to absorb x-rays as they travel toward the image detector 44, leading to the problems described above.

With reference to FIG. 4, m the event that the semiconductor device 20 is in a "flipped over" state on the tray 22, with substantial absorption of x-ray energy by the material between the active region 24A of the silicon body 24 and the source of x-rays 42, the problem described above is generally avoided (see FIG. 5, even for x-rays passing between the solder balls 36). However, complete structures commonly include semiconductor devices 20 on both sides of a printed circuit board 40, combining the orientation of FIG. 1 and 4 in a single structure, so that the problem described above with regard to the orientation of FIG. 1 continues to exist.

While x-ray inspection system suppliers mention use of a filter in the x-ray process, no systematic approach is indicated for dealing with this problem.

What is needed is an x-ray system wherein the silicon body of a device being x-rayed absorbs minimal x-ray energy, while copper layers and solder balls of the device are highly absorbent of x-ray energy so that proper imaging of the device is provided.

DISCLOSURE OF THE INVENTION

The present apparatus for irradiating a device with x-rays comprising a first material and a second material associated therewith includes a source of x-rays, a filter for receiving x-rays from the source of x-rays and allowing transmission of x-rays therethrough to the device, the filter having an atomic number greater than the atomic number of the second material of the device, and an x-ray imager for receiving x-rays from the device.

The present invention is better understood upon consideration of the detailed description below, in conjunction with the accompanying drawings. As will become readily apparent to those skilled in the art from the following description, there is shown and described of this invention simply by way of the illustration of the best mode to carry out the invention. As will be realized, the invention is capable of other embodiments and its several details are capable of modifications and various obvious aspects, all without departing from the scope of the invention. Accordingly, the drawings and detailed description will be regarded as illustrative in nature and not as restrictive.

BRIEF DESCRIPTION OF THE DRAWINGS

The novel features believed characteristic of the invention are set forth in the appended claims. The invention itself, however, as well as said preferred mode of use, and further objects and advantages thereof, will best be understood by reference to the following detailed description of an illustrative embodiment when read in conjunction with the accompanying drawings, wherein:

BEST MODE(S) FOR CARRYING OUT THE INVENTION

Reference is now made in detail to a specific embodiment of the present invention which illustrates the best mode presently contemplated by the inventors for practicing the invention.

Initially, reference is made to the article "Filter Optimization for X-ray Inspection of Surface-Mounted ICs", pages 377–379, by Richard C. Blish II, Susan Xi, and David Ledtonen, published April, 2002 at IEEE 40th Annual International Reliability Physics Symposium, Dallas, Texas, which material is herein incorporated by reference.

Figure 1:
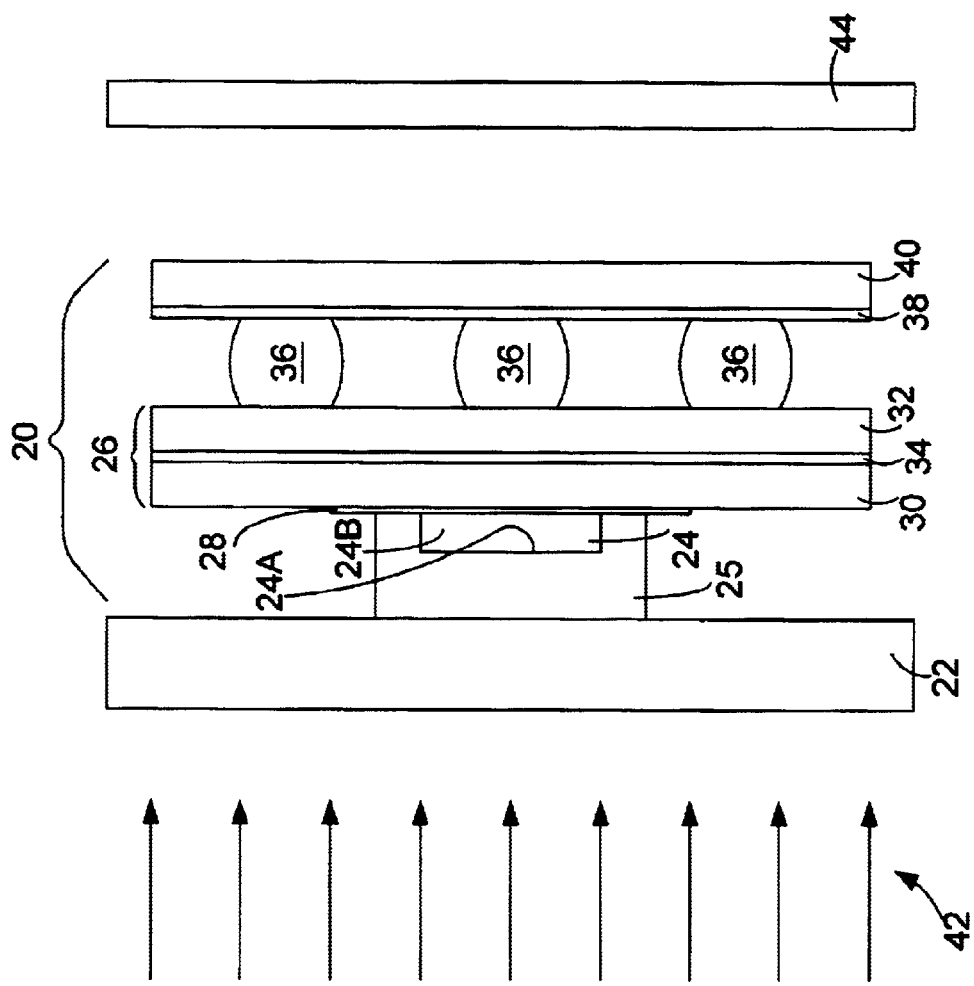
FIG. 1 is a sectional view of a semiconductor device undergoing x-ray examination in a typical prior art process.
Figure 6:
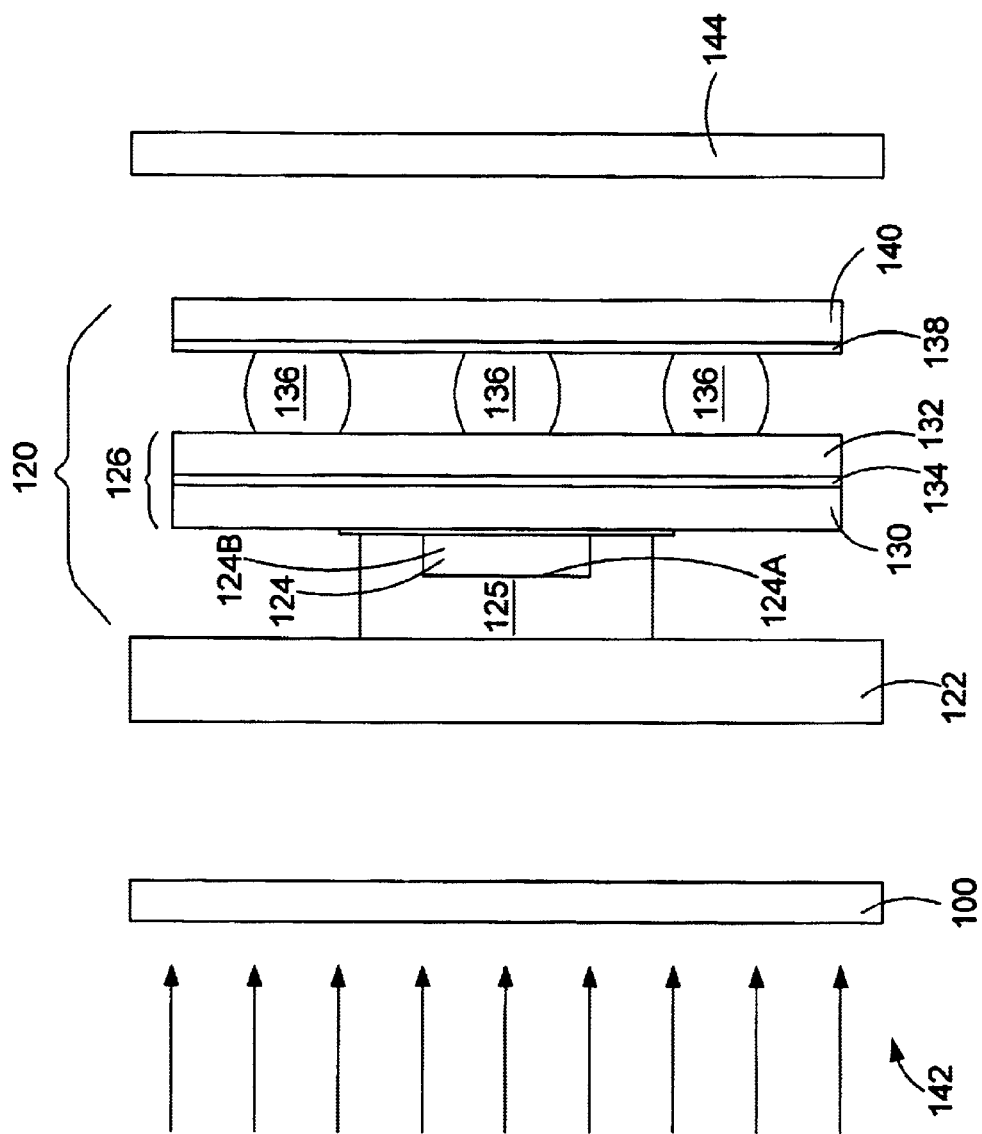
FIG. 6 is a sectional view of a semiconductor device undergoing x-ray examination in a an embodiment of the present invention.

FIG. 6 is similar to FIG. 1, but further including a filter 100 as will now be described As shown in FIG. 6 (rotated 90 degrees clockwise from a conventional orientation of elements therein), a semiconductor device 120 is placed on an inspection tray 122 of for example polyimide material. This typical semiconductor device 120 includes a silicon body 124 having a protective coating 125 of molding compound (in FIG. 6 shown lying on the tray 122), the silicon body 124 having an active region 124A and an inactive region 124B secured to a substrate 126 by a silver-organic material adhesive 128 (wire bonds connecting silicon body 124 and substrate 126 not shown). The substrate 126 includes organic portions (for example dielectric layers 130, 132) and patterned copper layers (one shown at 134), which copper layer 134 communicates with the active region 124A of the silicon body 124 (approximately 1 µm in thickness and oriented most adjacent the tray 122) and solder balls 136 (commonly lead/tin but which may consist of a lead-free composition, usually tin-rich) which connect to a layer of copper traces 138 on an organic material (for example polyimide, epoxy, polyethylene, or glass fiber) printed circuit board 140. As previously described, it will be understood that the particular configuration of the semiconductor device 120 is for purposes of illustration, and that such device 120 may be configured in a wide variety of ways, including for example a number of levels of copper layers 134 and dielectric layers 130, 132, with appropriate vias connecting the copper layers.

As in the previous example, the following typical thicknesses are given:

| | |
|---|---|
| Tray 122: | 400 µm |
| Molding Compound 125: | 300 µm |
| Silicon body 124: | 200 µm (including 1 µm active region) |
| Silver-organic adhesive 128: | 30 µm |
| Dielectric layer 130: | 200 µm |
| Copper layer 134: | 50 µm |
| Dielectric layer 132: | 200 µm |
| Solder balls 136: | 400 µm |
| Copper layer 138: | 50 µm |
| Printed circuit board 140: | 200 µm |

In the present embodiment, a filter 100 in the form of a zinc foil is positioned between a source of x-rays 142 and the tray 122, such plate 100 having a thickness of for example 300 µm.

Figure 2:
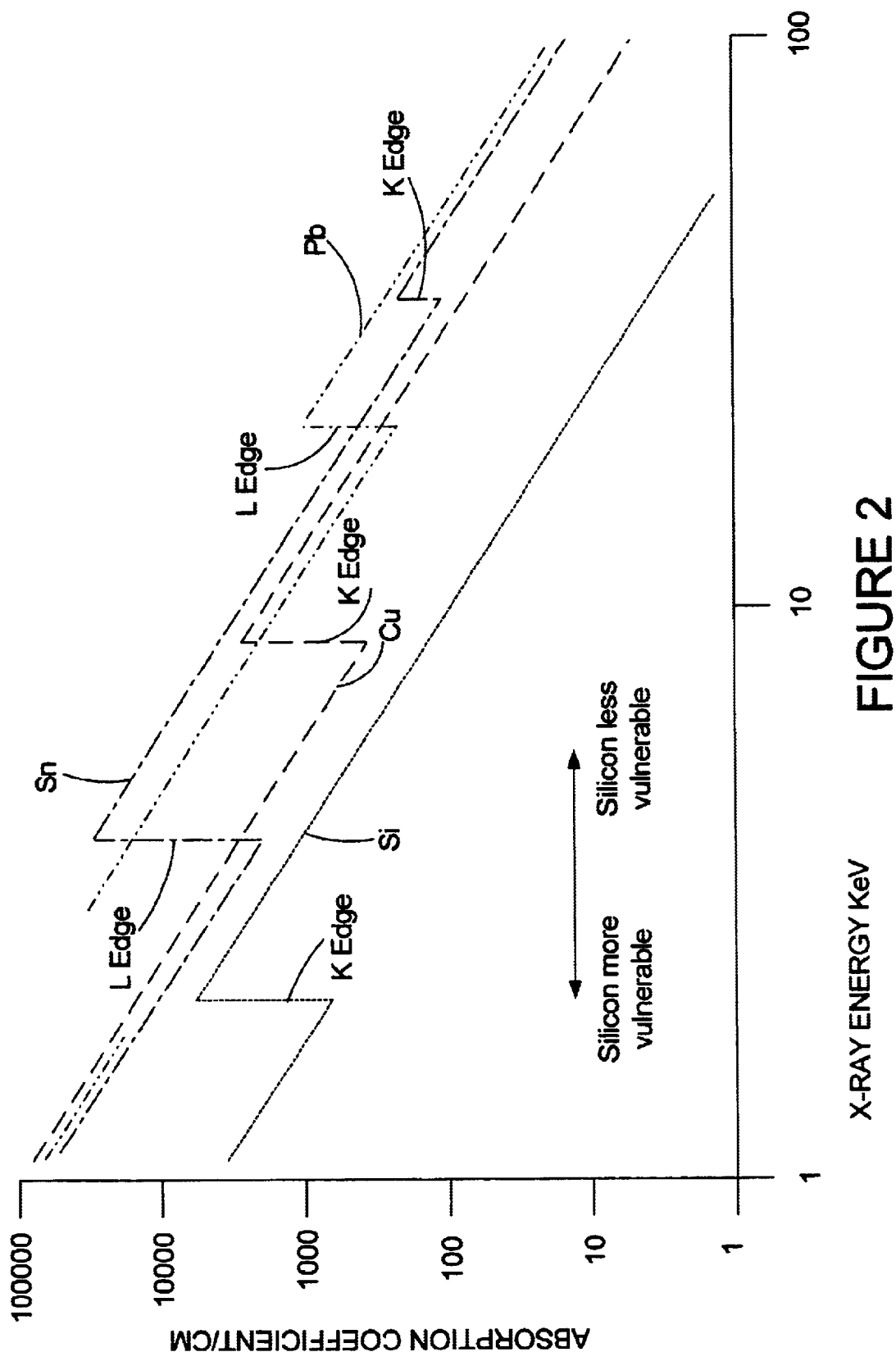
FIG. 2 is a graph showing x-ray absorption coefficient vs. x-ray energy level for silicon, copper, tin and lead, with both axes on a logarithmic scale.
Figure 7:
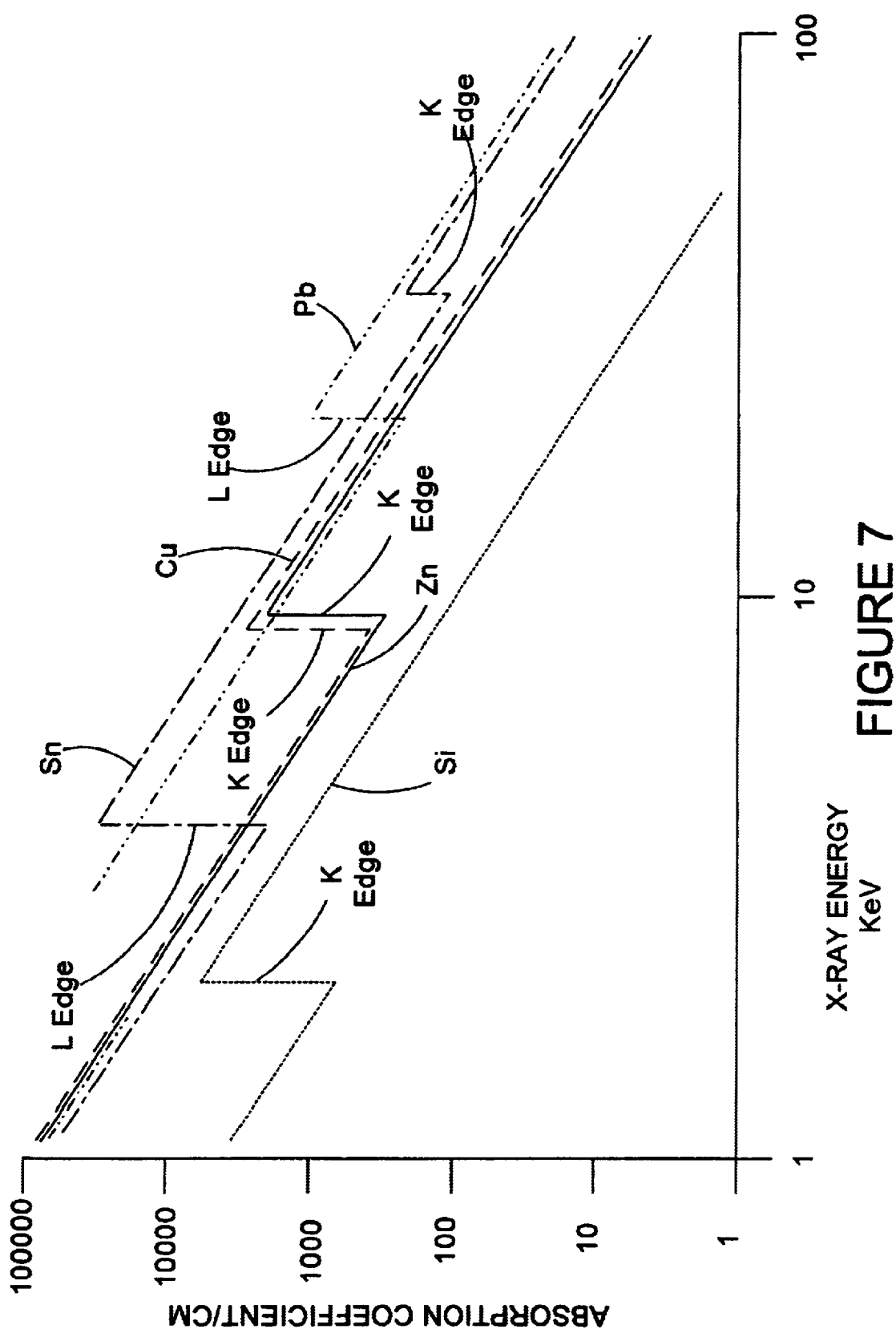
FIG. 7 is a graph showing x-ray absorption coefficient vs. x-ray energy level for silicon, copper, tin, lead and zinc, with both axes on a logarithmic scale.

FIG. 7 is a graph showing x-ray absorption coefficient vs. x-ray energy level for silicon, copper, tin and lead (similar to FIG. 2), but also showing x-ray absorption coefficient vs. x-ray energy level for zinc. Zinc has an atomic number of 30, one greater than the atomic number of copper, which results in the K edge of zinc lying to the right of the K edge of copper, i.e., at a higher energy level (FIG. 7). The importance of this feature will be described further on.

Figure 3:
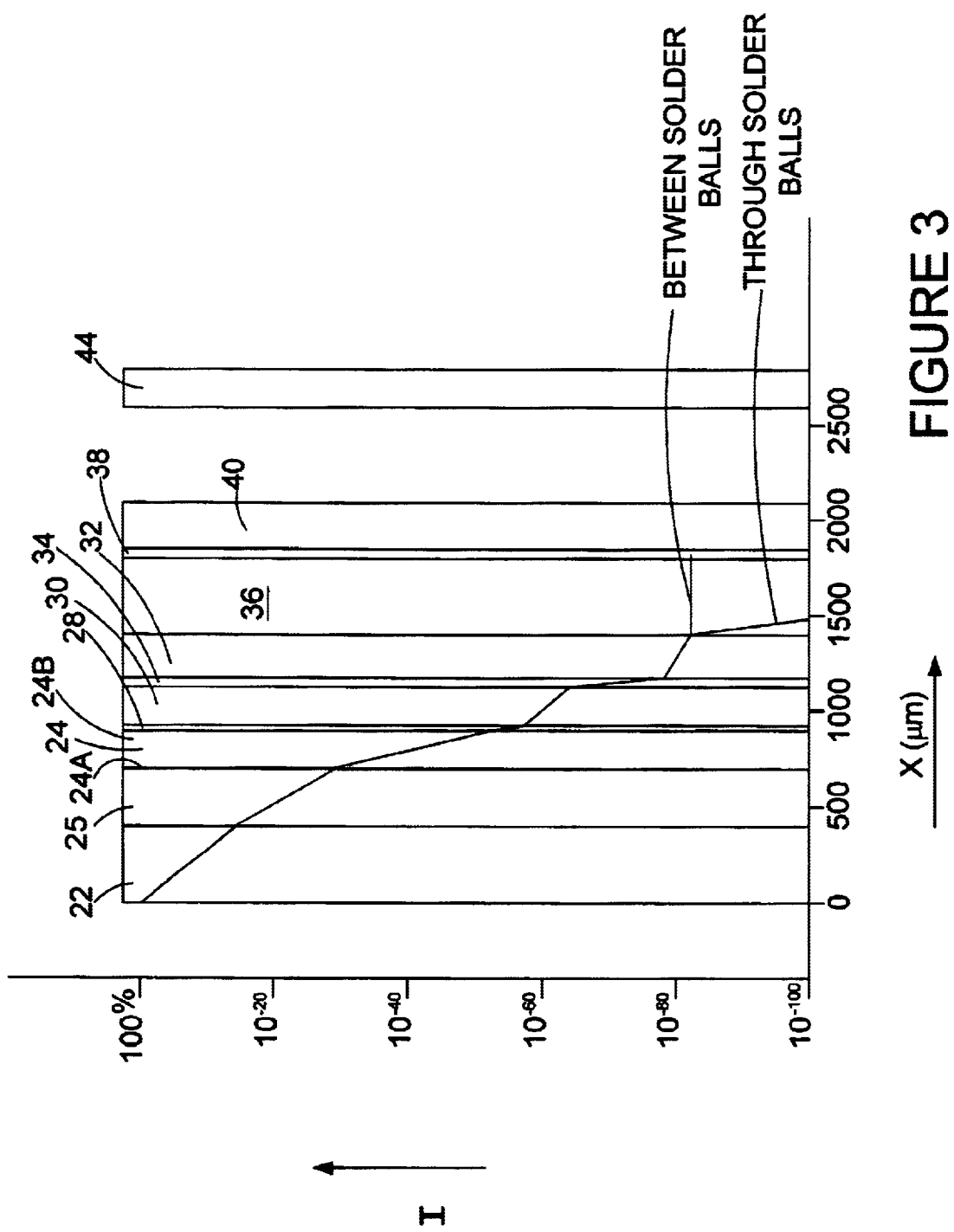
FIG. 3 is a graphical representation of the structure of FIG. 1, showing absorption of x-ray energy at the 3 KeV energy level.
Figure 4:
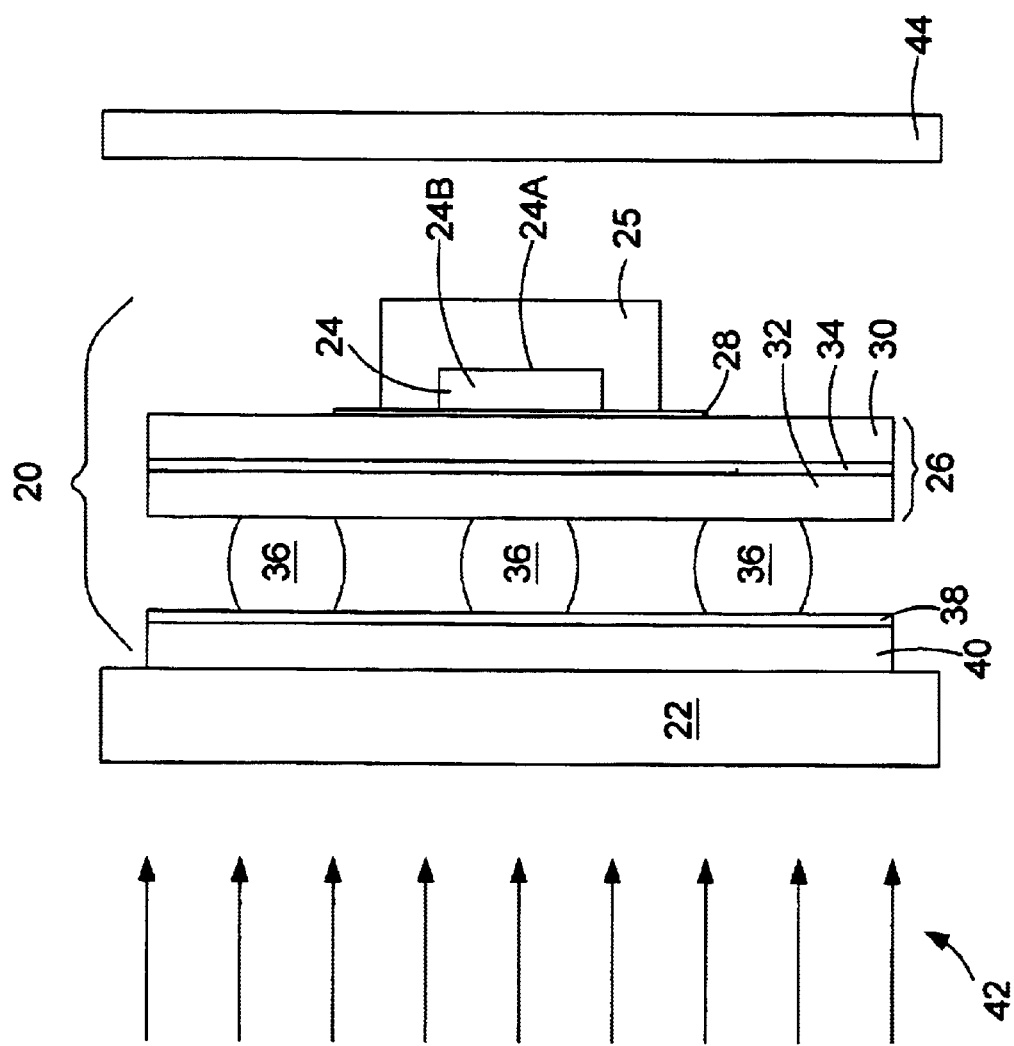
FIG. 4 is a sectional view similar to that shown in FIG. 1, but with the semiconductor device in a "flipped over" state relative to the tray.
Figure 5:
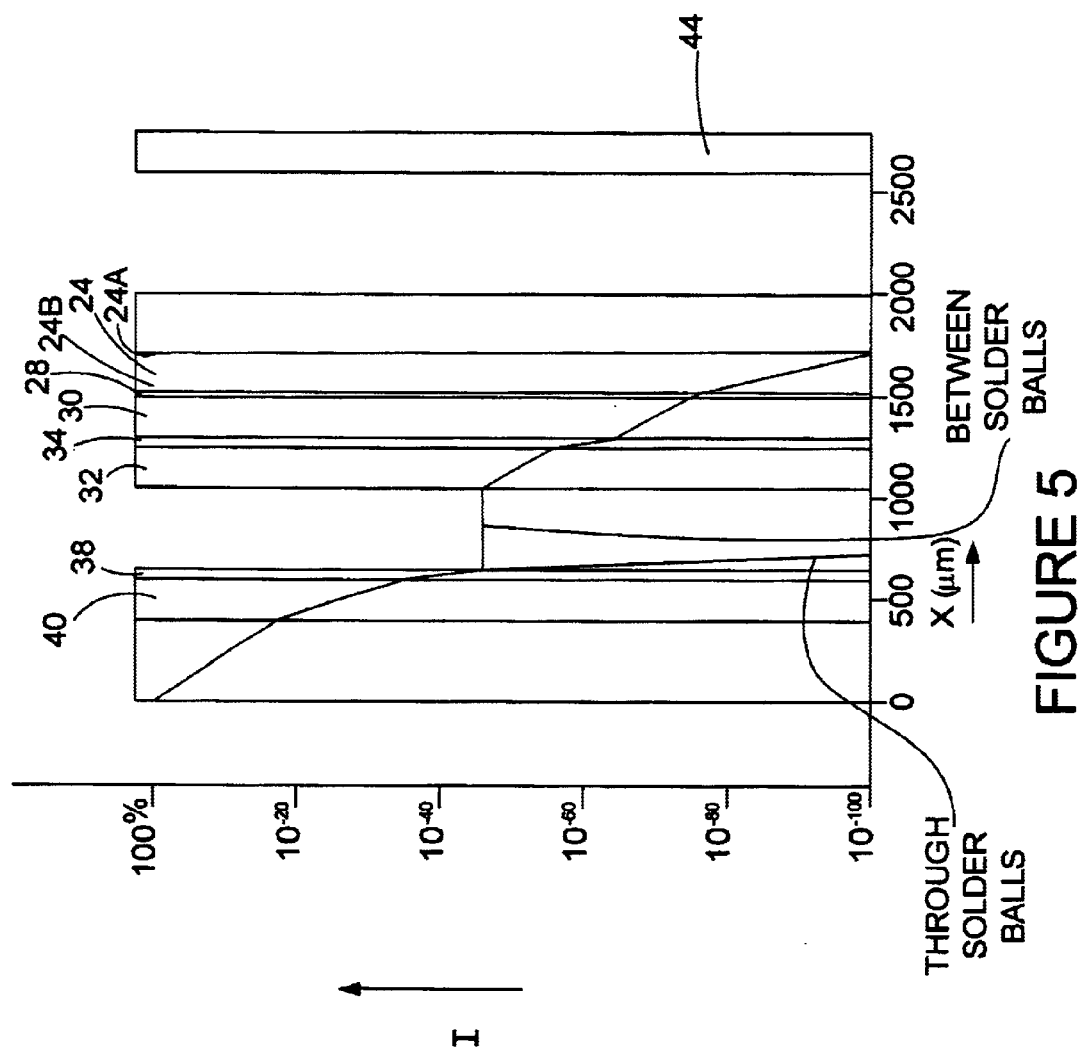
FIG. 5 is a graphical representation of the structure of FIG. 1, showing absorption of x-ray energy at the 3 KeV energy level.
Figure 8:
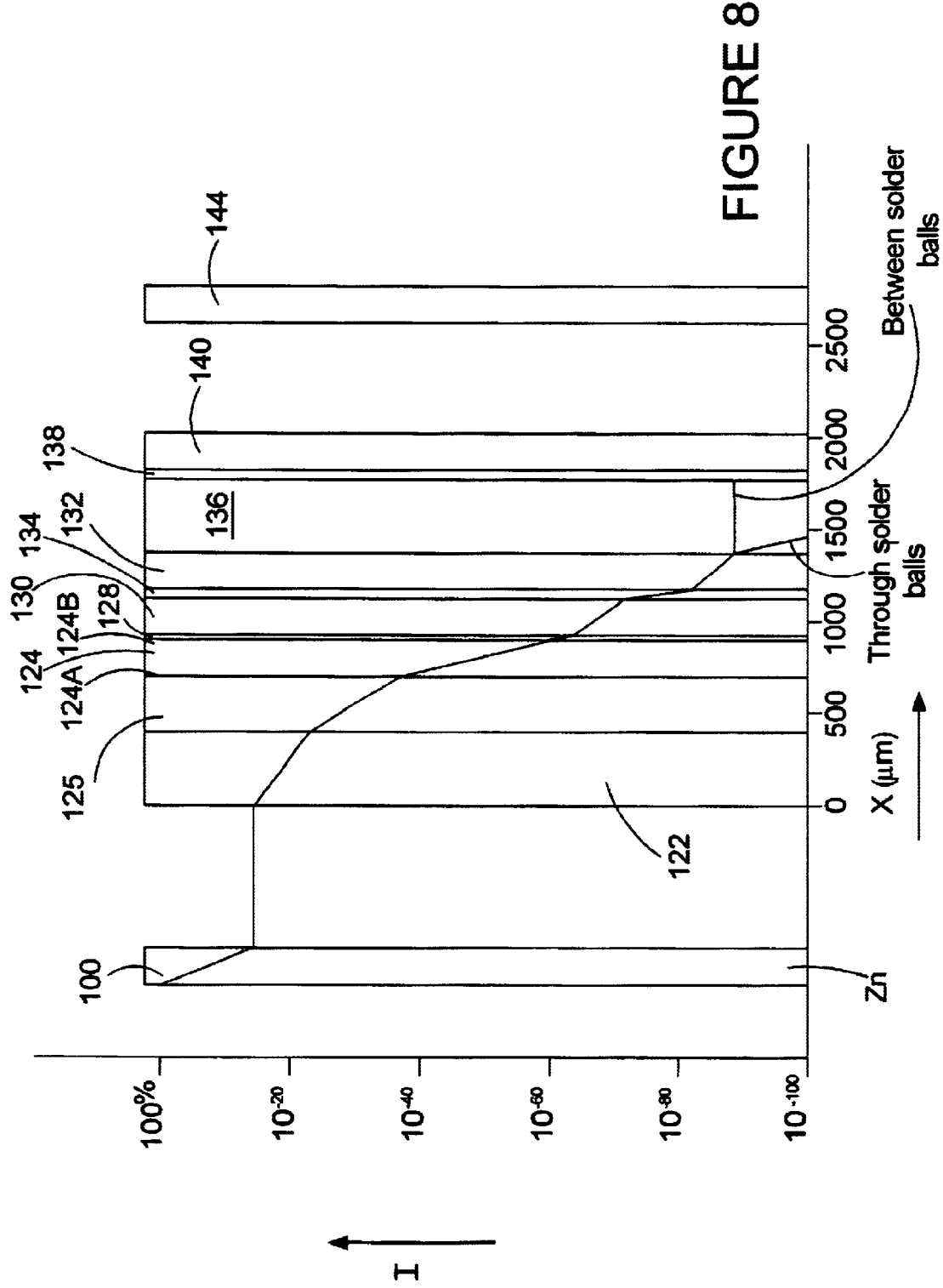
FIG. 8 is graphical representations of the structure of FIG. 6, showing absorption of x-ray energy at the 3 KeV energy level.
Figure 9:
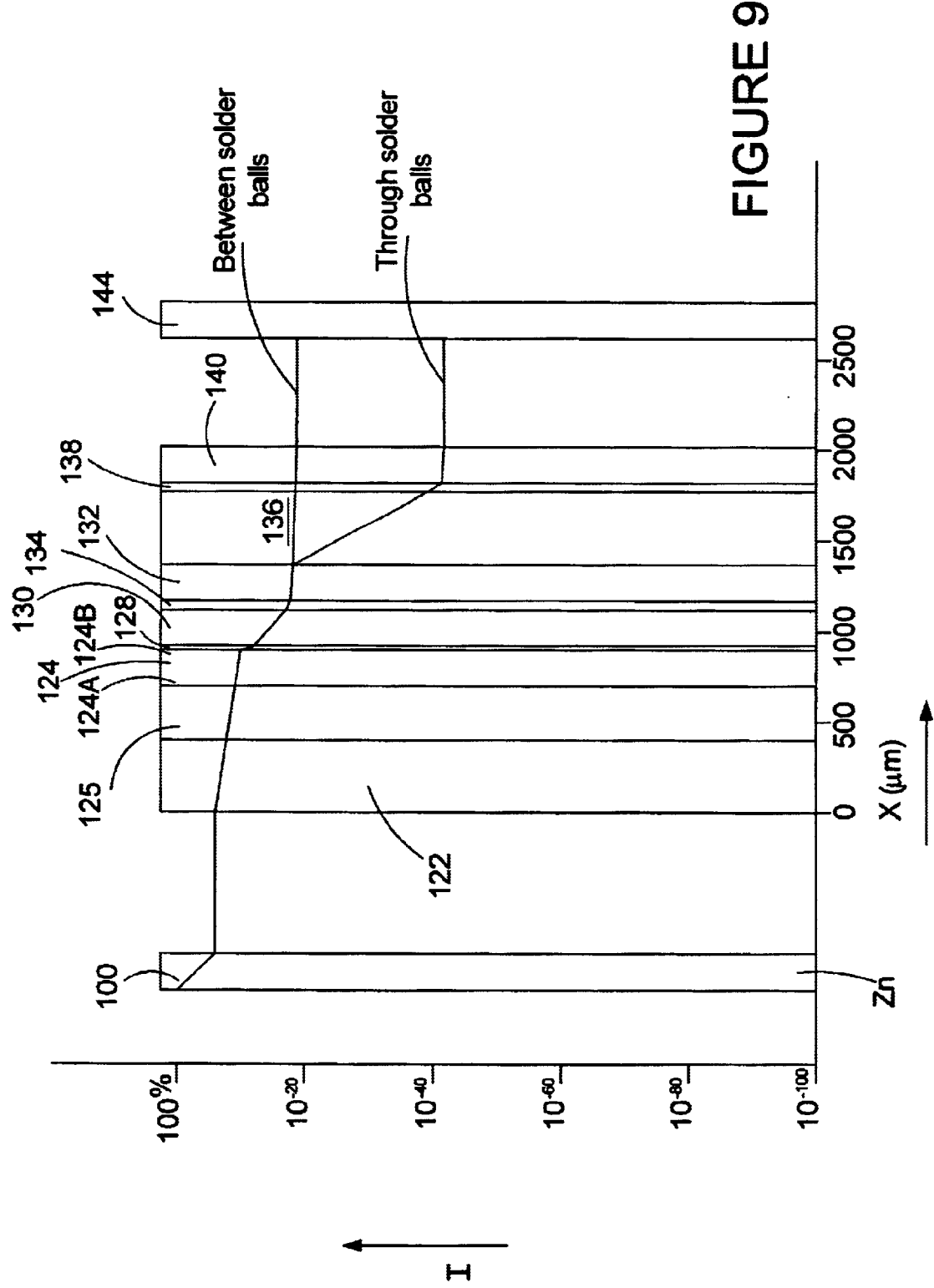
FIG. 9 is graphical representations of the structure of FIG. 6, showing absorption of x-ray energy at the 9 KeV energy level.

During x-ray inspection, x-rays including a wide range of energy levels are provided from the source 142 through the tray 122 and into and through the semiconductor device 120. FIGS. 8 and 9 are graphical representation of the structure of FIG. 6 for x-ray energy levels of 3 KeV and 9 KeV respectively. With reference to FIG. 8, for x-ray energy at the 3 KeV level, i.e., that x-ray energy level wherein silicon has a high coefficient absorption, the zinc filter 100 causes the intensity of the x-ray bean to drop significantly prior to passing through the tray 122 and reaching the silicon body 124. Thus, the intensity of the x-ray beam presented to the silicon body 124 is substantially lower th in the prior art, and the change in intensity of the x-ray beam through the silicon body 124, corresponding to the absorption of x-ray energy by the silicon body 124, is substantially lower than in the prior art, due to the inclusion of the zinc filer 100 (compare FIG. 3 and 8). With this low level of absorption of x-ray energy by the silicon body 124 as compared to the prior art, the problem of ionization of the silicon body 124 in the active region 124A, as described above, is overcome. Meanwhile, the thin adhesive 128 and dielectric layer 130, having low absorption, allow significant x-ray intensity to reach the high absorption copper layer 134. After a high degree of absorption by the copper layer 134, x-ray energy passes through the dielectric layer 132 (low absorption), solder balls 136 (high absorption), copper layer 138 (high absorption) and printed circuit board 140 (low absorption), so that the copper layers and solder balls are properly imaged as a radiograph at the image detector 144 at the 3 KeV x-ray energy level.

FIG. 9 is a graphical representation similar to that of FIG. 8, but for the 9 KeV x-ray energy level. At this energy level, absorption by the zinc filter 100 is lower than as shown in FIG. 8 but is still considerable (see absorption coefficients of zinc for various x-ray energy levels in FIG. 7). Meanwhile, the silicon body 124 is substantially less absorbing at this energy level (again see FIG. 7), so that the problem of ionization of silicon is again avoided. Meanwhile, because the atomic number of the zinc filter 100 is greater than the atomic number of copper (in this case one atomic number greater), resulting in the offset in the K lines of copper and zinc in the region of 9 KeV of x-ray energy as shown, the copper is substantially more energy absorbing than the zinc at this energy level, so that the zinc filter 100 transmits a significant amount of x-ray energy to the copper (which at this energy level has significant absorption), providing for highly effective imaging of the copper layers.

An important factor in being able to properly image a layer (copper in the examples given) is the selection of filter material with an atomic number greater than a specified layer to be imaged. This determines the offset between the K lines of the layer to be imaged and filter material (greater difference in these numbers determining greater offset between these K lines, and vice versa), which provides a "window" between these K lines at approximately the 9 KeV energy level, so that proper imaging at this energy level is achieved. It is to be noted that this is achieved along with proper shielding of the silicon body by the filter material as described above. It will be understood that this approach is not limited to copper and zinc, but is highly useful in imaging a wide variety of materials, wherein the material of the filter has a slightly higher atomic number than the material to be imaged. For example, in the situation where copper is to 4he be imaged, filter 100 may with advantage be made up of or include a material having an atomic number ranging from 30 through 35 inclusive, i.e. zinc (atomic number 30), gallium (atomic number 31), germanium (atomic number 32), arsenic (atomic number 33), selenium (atomic number 34), or bromine (atomic number 35).

While this approach provides proper imaging of the copper, which is normally difficult or impossible to achieve, imaging of the thick solder balls, which are an import target in the imaging process, is easily accomplished in the normal approach described above, i.e., regardless of the presence or absence of a filter of a particular atomic number.

The foregoing description of the embodiment of the invention has been presented for purposes of illustration and description. It is not intended to be exhaustive or to limit the invention to the precise form disclosed. Other modifications or variations are possible in light of the above teachings.

The embodiment was chosen and described to provide the best illustration of the principles of the invention and its practical application to thereby enable one of ordinary skill of the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. An apparatus for imaging a first material of a device, the device comprising said first material and a second material, said apparatus comprising:

a source of x-rays;

a filter for receiving x-rays from the source of x-rays and allowing transmission of x-rays therethrough to the device;

the filter material having an atomic number greater than the atomic number of the first material; and an x-ray detector for receiving x-rays from the device.

2. The apparatus of claim 1 wherein the second material is semiconductor material.

3. The apparatus of claim 2 wherein the semiconductor material comprises silicon.

4. The apparatus of claim 3 wherein the silicon contains an active region.

5. The apparatus of claim 4 wherein the first material comprises copper.

6. The apparatus of claim 5 wherein the filter material has an atomic number in the range of from 30 to 35 inclusively.

7. The apparatus of claim 6 wherein the filter material comprises zinc.

8. An apparatus for imaging a first material of a device, the device comprising copper and a second material, said apparatus comprising:

a source of x-rays;

a filter for receiving x-rays from the source of x-rays and allowing transmission of x-rays therethrough to the device;

the filter material having an atomic number greater than the atomic number of copper; and an x-ray detector for receiving x-rays from the device.

9. The apparatus of claim 8 wherein the second material comprises silicon.

10. The apparatus of claim 9 wherein the silicon contains an active region.

11. The apparatus of claim 10 wherein the filter material has an atomic number in the range of from 30 to 35 inclusively.

12. The apparatus of claim 11 wherein the filter material comprises zinc.

13. The apparatus of claim 12 wherein the device comprises a third material comprising lead.

14. The apparatus of claim 12 wherein the device comprises a third material comprising tin.

15. The apparatus of claim 12 wherein the device comprises a third material comprising a lead/tin mixture.

* * * * *

UNITED STATES PATENT AND TRADEMARK OFFICE
CERTIFICATE OF CORRECTION

PATENT NO. : 6,751,294 B1
DATED : June 15, 2004
INVENTOR(S) : Richard C. Blish II et al.

It is certified that error appears in the above-identified patent and that said Letters Patent is hereby corrected as shown below:

Column 1,
Line 17, "in on" should read -- inspection --;
Line 17, "f" should read -- futherance --;
Line 23, "In" should read -- in --;
Line 38, "illusion" should read -- illustration --;
Line 41, "cam" should read -- contain --;
Line 63, "been" should read -- between --;

Column 2,
Line 16, "sen" should read -- seen --;
Line 42, "$\mu$x" should read -- -$\mu$x --;
Line 57, "m" should read -- in --;

Column 4,
Line 8, "described" should read -- described. --;

Column 5,
Line 3, "th in" should read -- than --;
Line 53, "4he" should be deleted.

Signed and Sealed this

Twenty-first Day of December, 2004

JON W. DUDAS
*Director of the United States Patent and Trademark Office*